(12) United States Patent
Hawkins

(10) Patent No.: US 7,008,452 B2
(45) Date of Patent: Mar. 7, 2006

(54) DUAL DUROMETER ELASTOMER ARTIFICIAL DISC

(75) Inventor: John R. Hawkins, Cumberland, RI (US)

(73) Assignee: Depuy Acromed, Inc., Raynham, MA (US)

( * ) Notice: Subject to any disclaimer, the term of this patent is extended or adjusted under 35 U.S.C. 154(b) by 0 days.

(21) Appl. No.: 10/608,987

(22) Filed: Jun. 26, 2003

(65) Prior Publication Data
US 2005/0010290 A1    Jan. 13, 2005

(51) Int. Cl.
A61F 2/44    (2006.01)

(52) U.S. Cl. .................................. 623/17.11

(58) Field of Classification Search ............. 623/11.11, 623/16.11, 17.11, 17.13, 17.16, 23.5, 23.51, 623/23.52, 23.53, 14.12, 20.32, 20.34; 606/60, 606/61

See application file for complete search history.

(56) References Cited

U.S. PATENT DOCUMENTS

| | | | | |
|---|---|---|---|---|
| 3,867,728 A | * | 2/1975 | Stubstad et al. | 623/17.16 |
| 4,863,477 A | * | 9/1989 | Monson | 623/17.12 |
| 4,911,718 A | | 3/1990 | Lee et al. | |
| 5,123,926 A | * | 6/1992 | Pisharodi | 623/17.13 |
| 5,514,180 A | * | 5/1996 | Heggeness et al. | 623/17.16 |
| 5,545,229 A | | 8/1996 | Parsons et al. | |
| 5,645,597 A | * | 7/1997 | Krapiva | 606/61 |
| 5,674,294 A | * | 10/1997 | Bainville et al. | 623/17.16 |
| 5,702,450 A | * | 12/1997 | Bisserie | 623/17.16 |
| 5,824,094 A | | 10/1998 | Serhan et al. | |
| 5,888,226 A | * | 3/1999 | Rogozinski | 623/17.16 |
| 6,019,760 A | * | 2/2000 | Metz-Stavenhagen et al. | 606/61 |
| 6,132,465 A | * | 10/2000 | Ray et al. | 623/17.16 |
| 6,368,350 B1 | | 4/2002 | Erickson et al. | |
| 6,533,817 B1 | * | 3/2003 | Norton et al. | 623/17.16 |
| 6,554,867 B1 | * | 4/2003 | Joos | 623/23.5 |
| 6,592,624 B1 | * | 7/2003 | Fraser et al. | 623/17.16 |
| 6,602,291 B1 | * | 8/2003 | Ray et al. | 623/17.11 |
| 6,689,170 B1 | * | 2/2004 | Larsson et al. | 623/23.53 |
| 6,726,720 B1 | * | 4/2004 | Ross et al. | 623/17.13 |
| 6,802,863 B1 | * | 10/2004 | Lawson et al. | 623/17.16 |
| 2002/0082701 A1 | * | 6/2002 | Zdeblick et al. | 623/17.16 |
| 2003/0012331 A1 | | 1/2003 | Trieu | |
| 2003/0045940 A1 | * | 3/2003 | Eberlein et al. | 623/17.16 |
| 2004/0054413 A1 | * | 3/2004 | Higham et al. | 623/17.16 |
| 2004/0133278 A1 | * | 7/2004 | Marino et al. | 623/17.14 |
| 2004/0143332 A1 | * | 7/2004 | Krueger et al. | 623/17.14 |

\* cited by examiner

Primary Examiner—Eduardo C. Robert
Assistant Examiner—Anu Ramana
(74) Attorney, Agent, or Firm—Thomas M. DiMauro

(57) ABSTRACT

An intervertebral motion disc comprising core material surrounded by a non-resorbable outer shell having a sidewall surrounding the core, wherein the sidewall of the outer shell has a hardness of more than 80 Shore A.

25 Claims, 3 Drawing Sheets

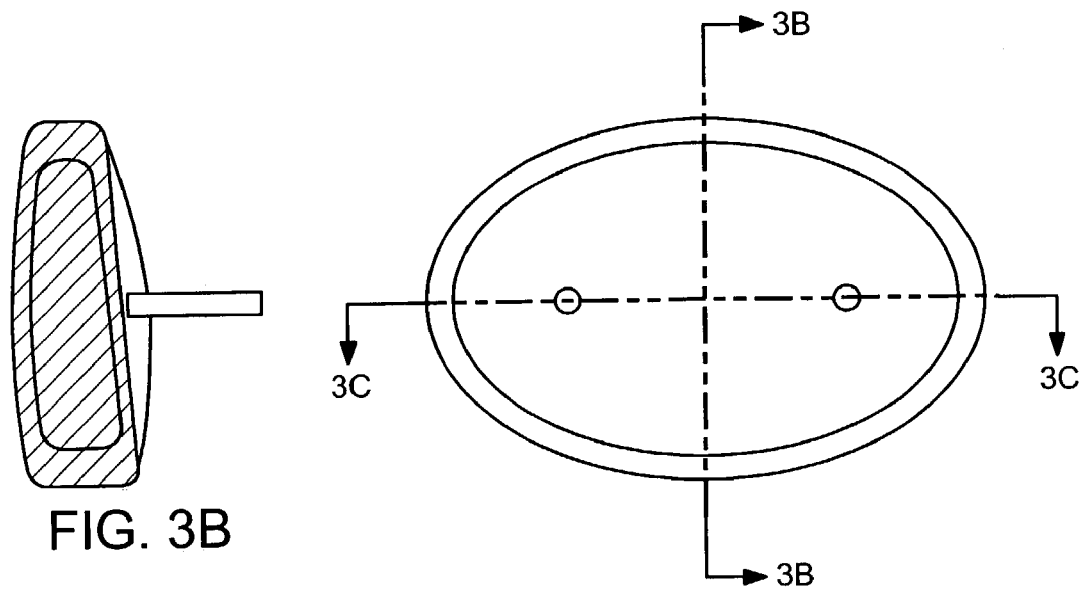
FIG. 3B
FIG. 3A
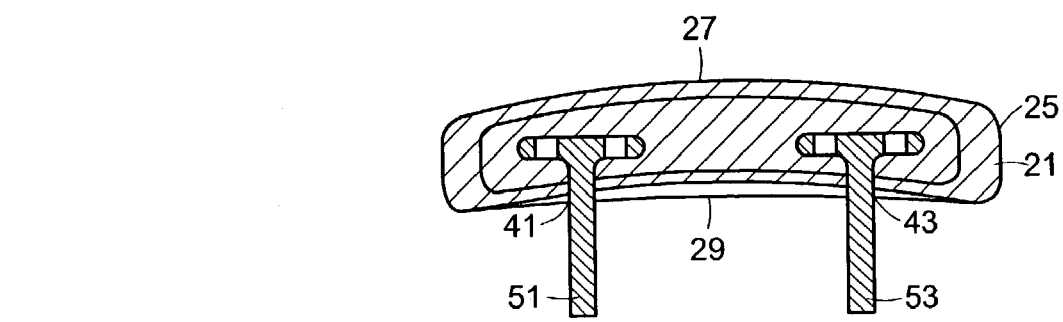
FIG. 3C
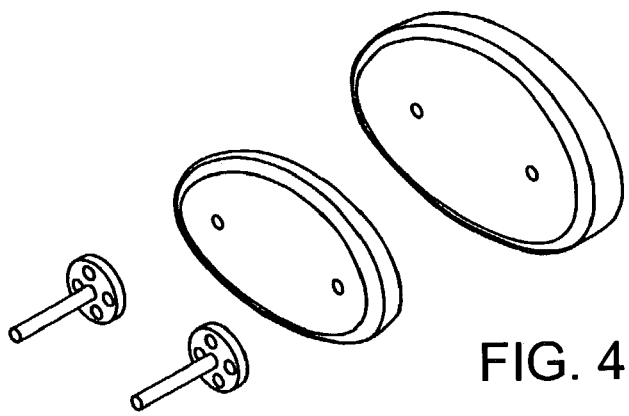
FIG. 4

DUAL DUROMETER ELASTOMER ARTIFICIAL DISC

BACKGROUND OF THE INVENTION

In a normal spine, a healthy intervertebral disc can compress about 1 mm when subjected to an axial load of 750 pounds force (3.4 kN). This ability to compress in response to axial loads provides the spine with an effective shock absorber against high loads.

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

Many prosthetic motion discs seek to mimic the flexion, extension and lateral bending of the natural disc by providing an articulating interface. For example, U.S. Pat. No. 6,368,350 ("Erickson") discloses a three-piece articulating motion disc providing two articulation surfaces. However, in order to minimize the amount of wear debris associated with the articulating interface, articulating motion discs tend to be made of very hard materials. Accoirdingly, articulating motion discs do not provide the shock absorbing function of a natural intervertebral disc.

Other motion discs seek to provide the shock absorbing function of the natural disc by providing a cushion within the prosthetic disc. For example, U.S. Pat. No. 5,824,094 ("Serhan") discloses a prosthetic motion disc comprising a rubber core member sandwiched between two metal endplates.

Another example of a cushion-type disc is disclosed in U.S. Pat. No. 4,911,718 ("Lee"). The Lee patent discloses a motion disc having a central core. See Lee at col. 3, lines 51–64. The core component of the Lee design seeks to mimic the nucleus pulposus of a natural disc, while the laminae seek to mimic the annulus fibrosus component of a natural disc, and the endplate components provide for anchorage to the adjacent endplates of the adjacent vertebral bodies.

In every design disclosed by Lee, the motion disc has a pair of endplates; and the outer laminae component comprises fibers.

Although the recognition in the Lee device of the need to mimic both the nucleus pulposus and annulus fibrosus components has its advantages, the provision in the Lee device of prosthetic endplates is problematic because it is known that the shear forces associated with natural vertebral movement will cause large shear stresses at the interfaces between the prosthetic endplates (on one hand) and the prosthetic nucleus pulposus and annulus fibrosus components (on the other hand).

Like the Lee patent, U.S. Pat. No. 5,545,229 ("Parsons") also discloses a motion disc having a pair of endplates, and intermediate components comprising an inner core and an outer ring. However, the outer ring of Parsons is designed so as to have a higher hardness than the inner core component. In particular, Parsons discloses that the outer ring is made of a "stiffer elastomeric material surrounding said central core to approximate the size and shape of a natural annulus fibrosus. See Parsons at col. 4, lines 7–16. Parsons specifically discloses preferred embodiments in which the core component has a hardness of between 20 and 70 shore-A, while the outer ring has a hardness of between 40 and 80 shore-A. Parsons further discloses that the device preferably uses the same elastomeric material in various degrees of stiffness for its various components (col. 4, lines 51–53). Table II discloses one particular embodiment in which the core is made of a block copolymer having a hardness of 35 shore-A, the outer ring is made of the same material having a hardness of 70 shore-A, the endplates are made of the same material having a hardness of 90 shore-A.

In every design disclosed by Parsons, the motion disc has a pair of endplates; and the outer ring is preferably no more than 80 shore-A.

The endplates are specifically designed to provide a mechanical interlock with the adjacent bone surface.

Although Parsons improves upon Lee by providing for a higher stiffness in the annulus fibrosus component, Parsons nonetheless retains the problematic endplate components of Lee.

Published U.S. patent application No. 2003/0023311 ("Trieu") discloses an artificial disc implant that is resistant to migration in and/or expulsion from an intervertebral disc space. In one form, the implant includes a load bearing elastic body surrounded in the disc space by an anchoring, preferably resorbable, outer shell. In certain forms, the elastic body is surrounded by a supporting member, such as a band or jacket, and the supporting member is surrounded by the outer shell. In another form of the invention, an implant is provided that has locking features and optional shape memory characteristics. In yet another aspect, nucleus pulposus implants are provided that have shape memory characteristics and are configured to allow short-term manual, or other deformation without permanent deformation, cracks, tears, breakage or other damage.

SUMMARY OF THE INVENTION

Applicant has noted that, although the dual hardness nature of each of Parsons and Lee is advantageous, each of Lee and Parsons appears to require an endplate component in their disclosed discs. However, since it is known that the shear forces acting upon an intervertebral disc are quite significant, the endplates components of Lee and Parsons may be subject to such high shear forces that they may separate from the remainder of the disc.

Therefore, in accordance with one aspect of the present invention, there is provided a prosthetic intervertebral disc comprising:

a) a central core material having an upper surface, a lower surface and a sidewall therebetween, and b) a non-resorbable outer shell having an inner surface surrounding the central core and contacting the upper surface, the lower surface and the sidewall of the core.

This invention is advantageous because the outer shell contacts the core along its sidewall surfaces as well, thereby providing more contact between these components, and reducing the chances of delamination therebetween.

In addition, Applicant has further noted that each of Lee, Parsons and Trieu must rely upon some tissue ingrowth in order to effectively work. In accordance with another aspect of the present invention, Applicant has developed an artificial disc that does not rely upon bony ingrowth for stability. In particular, Applicant has developed an artificial disc whose outer surface has a high coefficient of friction.

Therefore, in accordance with a first aspect of the present invention, there is provided a prosthetic intervertebral disc comprising:

a) a central core material, and b) a non-resorbable outer shell surrounding the central core, the outer shell having an upper wall having an upper outer surface, wherein the upper surface of the upper wall of the outer shell has a dry coefficient of friction against bone of at least 0.5.

This invention is advantageous because it does not rely upon bony ingrowth for stability.

Lastly, Applicant has further noted that Parsons prefers its annulus fibrosus component to have a hardness of no more than 80 Shore A. However, in this condition, elastomeric materials do not possess the elongation characteristics of the natural annulus fibrosus. In accordance with one aspect of the present invention, Applicant has developed an artificial disc whose sidewall has a hardness of more than 80 Shore A. In this condition, the elongation and stiffness characteristics of the sidewall more closely approximate the performance of the adjacent annulus fibrosus fibers and the vertebral body endplates.

Therefore, in accordance with a second aspect of the present invention, there is provided a prosthetic intervertebral disc comprising:

a) a central core material, and
b) an outer shell having a sidewall surrounding the core, wherein the sidewall of the outer shell has a hardness of more than 80 Shore A.

DESCRIPTION OF THE FIGURES

FIG. 3a discloses an upper view of the assembled disc of the present invention.

FIG. 3b discloses an anterior-posterior cross-section of the assembled disc of the present invention.

FIG. 3c discloses a lateral cross-section of the assembled disc of the present invention.

FIG. 4 discloses an exploded view of the disc of FIGS. 3a–3c.

DETAILED DESCRIPTION OF THE INVENTION

Figure 1:
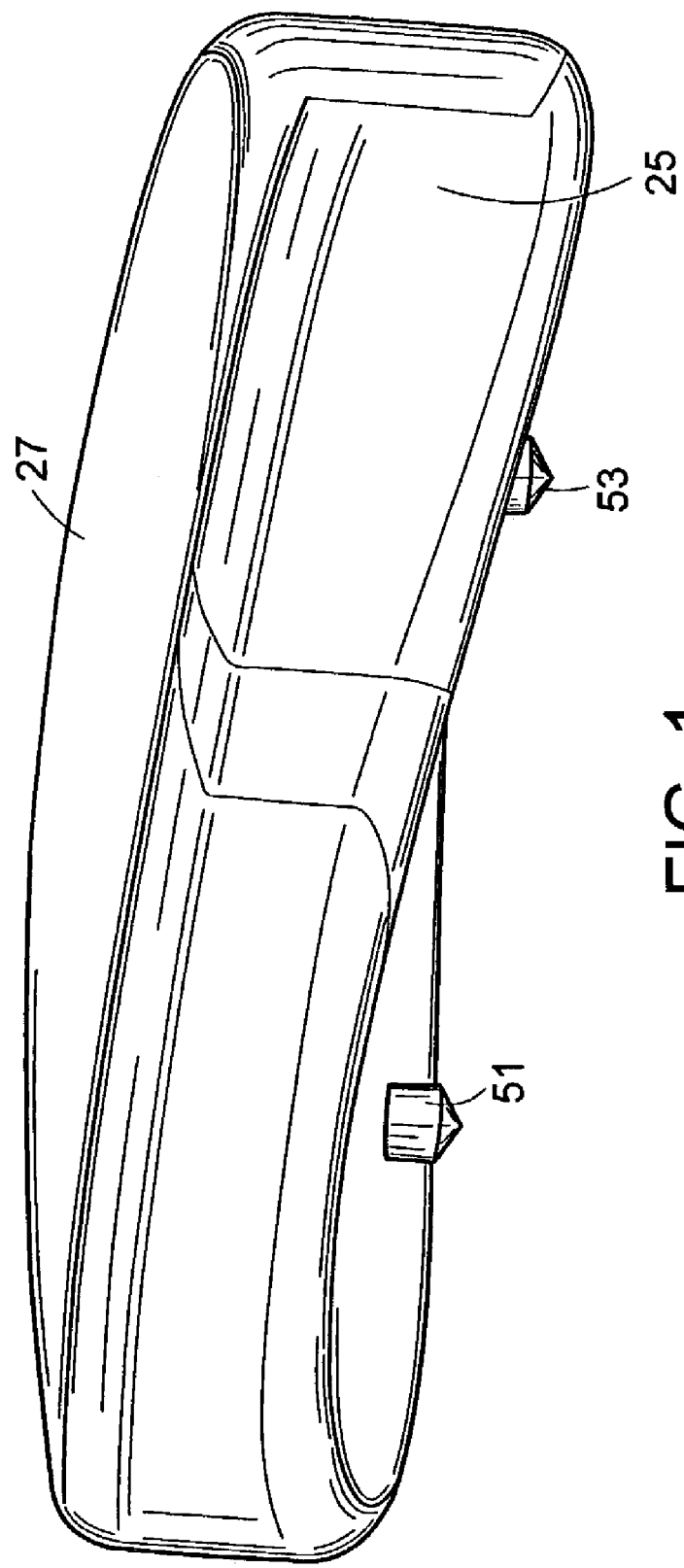
FIG. 1 discloses a perspective view of the disc of the present invention.
Figure 2B:
FIG. 2b discloses an anterior-posterior cross-section of the central core component of the present invention.
Figure 2A:
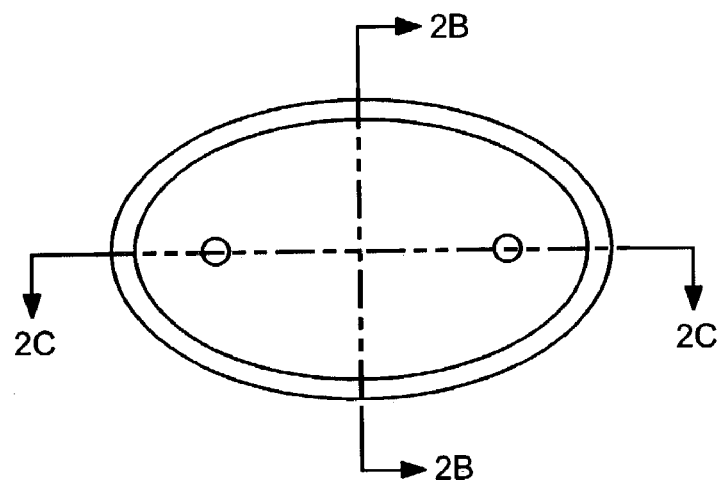
FIG. 2a discloses an upper view of the central core component of the present invention.
Figure 2C:
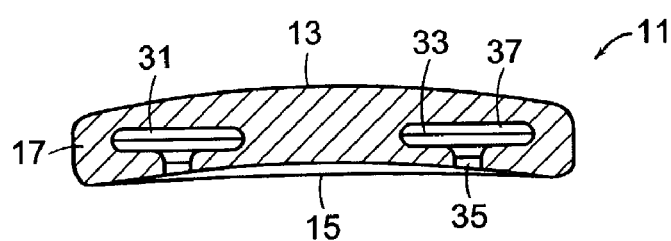
FIG. 2c discloses a lateral cross-section of the central core component of the present invention.

For the sake of clarity, "durometer" is the term of art used in the field for the hardness of an elastomeric material.

Now referring to FIGS. 1, 2a–c and 3a–c, there is provided an intervertebral disc 1 for insertion between opposed endplates of adjacent vertebral bodies, the disc comprising:

a) a central core material 11 having:
   an upper surface 13, a lower surface 15 and a peripheral sidewall 17 therebetween, and
   first 31 and second 33 recesses extending into the core from the lower surface 15, each recess forming a necked portion 35 and a cavity 37, b) a non-resorbable outer shell 21 having:
   an inner surface 23 surrounding the central core and contacting the upper surface, the lower surface and the sidewall of the core, and an outer surface 25 having an i) upper surface 27 adapted to contact a natural upper vertebral endplate and ii) a lower surface 29 adapted to contact a natural lower vertebral endplate, and
   first 41 and second 43 channels extending through the lower surface of the shell and opening onto the recesses of the core, c) first 51 and second 53 radio-opaque marker pins, each having a necked portion and a head portion, the necked portion being received in the corresponding channel of the shell and necked portion of the core, the head portion being received in the cavity portion of the core.

The prime function of the core is to provide shock absorbing qualities when the disc is under large axial loads and to transfer that load radially in the manner of a natural nucleus pulposus.

Preferably, the core is made of a material having an axial compression strength of at least 10 MPa, and a compression modulus of between 0.5 GPa and 20 GPa. Preferably, the core is made of a material having a durometer of between 20 and 60 Shore A, preferably between about 30 and 50 Shore A, more preferably between about 35 and 45 Shore A.

Preferred materials having these characteristics include thermoplastic elastomers and silicone.

Preferably, the dimensions of the core are such that they mimic the dimensions of the nucleus pulposus in the natural disc that the disc of the present invention is replacing. Accordingly, in some embodiments, the core has a convex outer surface, and may be spherical. In some embodiments, as in FIG. 2, the upper and lower surfaces of the core are relatively flat and the core has an elliptical saggital cross-section.

The prime functions of the shell are to accept the load transfer by the core in the manner in which the annulus fibrosus accepts the load transferred from the nucleus pulposus.

Because the function of the shell is to accept load in the manner of the annulus fibrosus, preferably, the shell is made of a material having a high tensile strength. Preferably, the shell is made of a material having a durometer of between 70 and 100 Shore A, preferably between more than 80 Shore and 100 Shore A, more preferably between about 85 and 95 Shore A. The higher relative durometer of the shell enables it to act as a constraining force against the outward expansion of the core.

Preferred materials having these characteristics include elastomers including polyurethane and silicone.

Preferably, the lateral geometry of the shell is such that it mimics the geometry of the annulus fibrosus in the natural disc that the disc of the present invention is replacing. Accordingly, in some embodiments, the shell is kidney shaped and has a convex anterior surface, and a concave posterior surface. In some embodiments, as in FIG. 2, the upper and lower surfaces of the shell are relatively flat and the shell has an elliptical saggital cross-section.

In some embodiments, the upper surface of the shell has a convex shape and the lower surface of the shell has a concave shape.

In some embodiments, the upper surface of the shell has a convex shape and the lower surface of the shell has a convex shape.

In some embodiments, the upper surface of the shell has a convex shape and the lower surface of the shell has a flat shape.

In some embodiments, the upper surface of the shell has a flat shape and the lower surface of the shell has a concave shape.

In some embodiments, the upper surface of the shell has a flat shape and the lower surface of the shell has a convex shape.

In some embodiments, the upper surface of the shell has a flat shape and the lower surface of the shell has a flat shape.

In these conditions, the surfaces are meant to mimic/match the anatomical geometry presented by the vertebral endplates during implantation surgery.

In some embodiments, the upper and lower surfaces of the shell component contact the respective upper and lower endplates. Preferably, these surfaces are contoured so as to conform to the shapes of the respective endplates. In some embodiments, the upper and lower surfaces are made so as to provide a high coefficient of friction ("COF") against the bony endplates. When these surfaces have such a high coefficient of friction, they suitably resist expulsion from the disc space under heavily loaded extension of the spine. Accordingly, the present invention need not rely upon the ingrowth of bony tissue or scar tissue into the shell (as do conventional devices) in order to stably remain in the disc space.

In some embodiments, the high coefficient of friction is provided chiefly by selecting a material having a high friction quality against bone, such as silicone. When such a material is selected, the surface roughness of the shell outer surface can be provided with a finished surface so that its surface roughness $R_{max}$ can be below about 0.15 mm.

Preferably, the materials and geometries of the core and shell components are selected so that, when combined, the combination has a mean axial stiffness of between 1000 N/mm and 3500 N/mm, and a mean torsional stiffness of between 0.8 Nm/degree and 3.0 Nm/degree. More preferably, the combination has a mean axial stiffness of between 2000 N/mm and 3000 N/mm, and a mean torsional stiffness of between 1 Nm/degree and 2 Nm/degree. When these properties are provided, the disc of the present invention will perform much like a natural interevertebral disc.

In some embodiments, the ratio of the length of the major axis of the core to the length of the major axis of the device is at least 75%, more preferably at least 85%. In this respect, the dimensions of the device vary somewhat from the FIG. 2 design of Parson and from the natural intervertebral disc (each of which having a ratio of about 50%. Accordingly, the core of the present invention occupies a much larger space than does the natural nucleus pulposus in the natural disc. The present inventor believes that the provision of a higher durometer shell than that provided by Parsons allows the lateral thickness of the shell to be reduced and so allows more shock absorbing core material to occupy the disc of the present invention.

In some embodiments, the disc of the present invention may have an intermediate layer provided between the core and shell components. In these embodiments, it is preferable to select a material having an intermediate durometer as well.

As shown in FIG. 1, in some embodiments, the device may further comprise a radio-opaque marker for enabling tracking of the device after surgery. In some embodiments, the marker is provided as a pin. In some embodiments, the radio-opaque marker is a titanium alloy, preferably Ti-6Al-4V alloy.

A preferred manufacturing method of the present invention allows a precise outer layer thickness and a precise inner core volume. The amount of cushion material is maximized to fill the anatomical cavity created during surgery while the amount of outer shell material is minimized to provide durability without impairing the motion of the disk.

With the use of support pins, a two-step or three-step molding process can be used to manufacture the invention.

In one embodiment, the first stage comprises forming the core material, while the second stage comprises forming the shell. The use of rigid metal marker pins to support the core during the second stage allows the full core to stand-off a precise distance from the walls of the second-stage mold. Thus, the invention is complete after two stages. In this way, the outer shell can preferably be as thin as 0.5 mm or as thick as 2 mm, and can possess a variable thickness around its periphery to provide for varying expansion of the core during use. This may be advantageous to the life of the device, and may more accurately reflect anatomical motion. In addition, the use of metal pins allows the present invention to be readily identified during medical imaging, as they are radio-opaque markers.

In another embodiment, the support pins are fully-cured elastomeric pins. These pins provide the same mechanical support during the molding process as the metal-based pins, but can not be as easily identified in medical imaging. The same design control over the shell thickness is provided in this embodiment.

In another embodiment, the support pins are part of the mold, or are molded onto the surface of the inner core. The full core is placed into the second molding cavity and pins protruding from the wall of the mold hold the core off the wall at a precise distance as the shell is molded on. The pinholes remaining in the shell after it has been molded are filled during a third-stage molding process or left as dimples. The pins can also be positive elastomer stand-offs that are molded onto the core in a secondary stage. A third stage then fills out the shell to make a unified outer shell. The same design control over the shell thickness is provided in this embodiment.

I claim:

1. A prosthetic intervertebral disc comprising:
   a) a central core material having an upper surface, a lower surface and sidewalls therebetween,
   b) a non-resorbable one piece outer shell having an inner surface surrounding the central core and contacting the upper surface, the lower surface and the sidewalls of the central core, wherein one of the upper and lower surfaces of the outer shell comprises a recess for receiving a pin, the recess extending from the upper or lower surface and extending into the central core and
   c) a pin extending from the upper or lower surface through the recess and received in a cavity in the central core
   wherein the outer shell has an upper wall having an upper surface having a dry coefficient of friction against bone of at least 0.5.

2. The disc of claim 1 wherein the non-resorbable shell has an outer surface, the outer surface having an i) upper surface adapted to contact a natural upper vertebral endplate and ii) a lower surface adapted to contact a natural lower vertebral endplate.

3. The disc of claim 2 wherein the upper surface of the shell is convex, and the lower surface of the shell is flat or concave.

4. The disc of claim 2 wherein the upper and lower surfaces of the shell are convex.

5. The disc of claim 1 wherein the outer shell further comprises an upper wall having a thickness, and a side wall having a thickness, wherein the thickness of the upper wall is lower than the thickness of the side wall.

6. The disc of claim 5 wherein the thickness of the sidewall approximates a thickness of the annulus fibrosus.

7. The disc of claim 1 further comprising:
c) an intermediate layer between the central core and the outer shell.

8. The disc of claim 1 having no intermediate layer between the core and the outer shell.

9. The disc of claim 1 further comprises:
c) a radio-opaque marker disposed within the outer shell or core.

10. The disc of claim 1 wherein the outer shell has a first hardness and the core has a second hardness, and wherein the first hardness is larger than the second hardness.

11. The disc of claim 1 wherein the upper surface of the upper wall of the outer shell has a surface roughness $R_{max}$ of no more than 0.15 mm.

12. The disc of claim 1 wherein the upper surface of the shell is convex, and the lower surface of the shell is flat or concave.

13. The disc of claim 1 wherein the upper and lower surfaces of the shell are convex.

14. The disc of claim 1 wherein the outer shell comprises silicone.

15. The disc of claim 1 wherein the outer shell further comprises a lower wall having a lower surface, the lower surface having a dry coefficient of friction against bone of at least 0.5.

16. The disc of claim 1 wherein the lower surface of the outer shell comprises a recess for receiving a pin.

17. The disc of claim 1 wherein at least one of the upper and lower surfaces of the shell is flat.

18. The disc of claim 1 wherein the central core and the outer shell are made of different grades of the same material.

19. The disc of claim 18 wherein the same material is silicone.

20. The disc of claim 1 wherein the central core has a first hardness and the sidewall of the outer shell has a second hardness, and wherein the first hardness is smaller than the second hardness.

21. The disc of claim 1 wherein the outer shell further comprises an upper wall having a first thickness, and a side wall having a second thickness, and wherein the first thickness is smaller than the second thickness.

22. The disc of claim 1 wherein the second thickness of the sidewall approximates a thickness of the annulus fibrosus.

23. The disc of claim 1 wherein the outer shell is elastomeric.

24. The disc of claim 23 wherein the elastomeric outer shell is selected from the group consisting of polyurethane and silicone.

25. The disc of claim 1 wherein the non-resorbable one piece outer shell has an inner surface that completely surrounds the central core.

* * * * *